United States Patent
Peng et al.

(10) Patent No.: US 8,944,256 B2
(45) Date of Patent: Feb. 3, 2015

(54) FILTER

(75) Inventors: Zhang Peng, Shenzhen (CN); Shi Xueyuan, Shenzhen (CN); Gao Zaixing, Shenzhen (CN); Xu Zhi, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 934 days.

(21) Appl. No.: 12/510,944

(22) Filed: Jul. 28, 2009

(65) Prior Publication Data

US 2010/0025321 A1 Feb. 4, 2010

(30) Foreign Application Priority Data

Jul. 30, 2008 (CN) .......................... 2008 1 0142711

(51) Int. Cl.
| | | |
|---|---|---|
| *B01D 29/92* | (2006.01) | |
| *B01D 29/33* | (2006.01) | |
| *B01D 29/15* | (2006.01) | |
| *B01D 19/00* | (2006.01) | |
| *B01D 29/11* | (2006.01) | |
| *C02F 1/00* | (2006.01) | |
| *B01L 3/00* | (2006.01) | |
| *G01N 1/10* | (2006.01) | |

(52) U.S. Cl.
CPC .... *B01D 19/0042* (2013.01); *B01D 2201/0453* (2013.01); *B01D 2201/043* (2013.01); *B01D 29/114* (2013.01); *B01D 2201/46* (2013.01); *B01L 3/502723* (2013.01); *G01N 1/10* (2013.01)
USPC ............................ 210/457; 210/459; 210/422

(58) Field of Classification Search
None
See application file for complete search history.

(56) References Cited

U.S. PATENT DOCUMENTS

| | | | | |
|---|---|---|---|---|
| 1,329,074 | A | * | 1/1920 | Cuno ............................ 137/577 |
| 4,673,501 | A | * | 6/1987 | Wells et al. ................... 210/406 |
| 5,010,776 | A | * | 4/1991 | Lucero et al. .............. 73/863.23 |
| 5,328,598 | A | | 7/1994 | Lohrl et al. |
| 5,616,172 | A | * | 4/1997 | Tuckerman et al. .............. 96/16 |
| 6,969,616 | B2 | | 11/2005 | Hirai et al. |
| 7,144,504 | B2 | * | 12/2006 | Tsai ........................... 210/416.2 |

FOREIGN PATENT DOCUMENTS

| | | |
|---|---|---|
| CN | 1131577 A | 9/1996 |
| CN | 2553803 Y | 6/2003 |

(Continued)

OTHER PUBLICATIONS

English Translation of Abstract for CN1131577, Sep. 25, 1996.
English Translation of Abstract for CN1816361, Aug. 9, 2006.
English Translation of Abstract for CN200957231, Oct. 10, 2007.
English Translation of Abstract for CN2553803, Jun. 4, 2003.

(Continued)

*Primary Examiner* — Katherine Zalasky
(74) *Attorney, Agent, or Firm* — Kory D. Christensen; Stoel Rives LLP (57) ABSTRACT

Disclosed is filter having a filter core, a top cover, a bottom cover, at least one first discharging pipe and at least one second discharging pipe, wherein the filter core has a slot through which a fluid to be filtered passes; the top cover and the bottom cover are respectively fixed to an upper portion and a lower portion of the filter core; an inner wall surface of the filter core, an inner wall surface of the top cover and an inner wall surface of the bottom cover define a filter cavity; the first discharging pipe has at least one first inlet through which the fluid flows in; the second discharging pipe has at least one second inlet through which the fluid flows in; and all the first inlets are situated above the second inlets in the gravity direction. The filter can realize the separation of two fluids.

14 Claims, 8 Drawing Sheets

(56) References Cited

FOREIGN PATENT DOCUMENTS

| CN | 1816361 A | 8/2006 |
|---|---|---|
| CN | 2836819 Y | 11/2006 |
| CN | 200957231 Y | 10/2007 |

OTHER PUBLICATIONS

English Translation of Abstract for CN2836819, Nov. 15, 2006.
International Search Report for Chinese Application No. 200810142711.7, Oct. 30, 2008.

* cited by examiner

FILTER

CROSS-REFERENCE

The present application claims priority to Chinese Patent Application 200810142711.7, filed on Jul. 30, 2008, which is hereby incorporated by reference in its entirety.

FIELD

The present invention relates to a filter to be used with a biochemical analyzer for filtering fluids.

BACKGROUND

In the intake line system of a biochemical analyzer, in order to prevent contaminants from entering into the line system that cause failure of a variety of elements in the system, it is common to employ an intake filter to filter the water entering into the tubes so that contaminant particles in the water can be filtered. In practice, however, it has been found that if a filter with relatively high precision (the filter core has a rather small slot) is used, then when the filter is in operation, numerous bubbles will be generated on the inner wall of the filter core due to the negative pressure within the filter. After these bubbles accumulate to some extent, they will enter into the line (e.g., quantitative sampling lines of the biochemical analyzer) with the water, and reduce the precision of quantitative sampling, thereby affecting the overall testing performance of the biochemical analyzer. In order to avoid generating numerous bubbles, it is necessary to employ a filter with relatively lower precision. In this case, however, the water filtered by the filter usually contains larger contaminant particles that will choke the precise hydraulic elements, thereby disabling the hydraulic path.

SUMMARY

One technical problem to be solved by some embodiments of the present invention is to overcome the deficiencies of the prior art, and to provide a filter which can both ensure the filtration precision and realize separation of two fluids.

The technical solution employed by some embodiments of the present invention to solve the technical problem is a filter comprising a filter core, a top cover, a bottom cover, at least one first discharging pipe and at least one second discharging pipe, wherein the filter core has a slot through which a fluid to be filtered passes; the top cover and the bottom cover are respectively fixed to an upper portion and a lower portion of the filter core; an inner wall surface of the filter core, an inner wall surface of the top cover and an inner wall surface of the bottom cover define a filter cavity; the first discharging pipe, which communicates with the filter cavity and is provided at the top cover, has at least one first inlet through which the fluid flows in; the second discharging pipe, which communicates with the filter cavity and is provided at the top cover or the bottom cover, has at least one second inlet through which the fluid flows in; and all the first inlets are situated above the second inlets in the gravity direction.

The second discharging pipe is provided at the top cover. The second discharging pipe extends downwards into the filter cavity, and the second inlet of the second discharging pipe is adjacent to the inner wall surface of the bottom cover.

The second discharging pipe extends downwards into the filter cavity, and the first inlet of the first discharging pipe is not lower than the inner wall surface of the top cover. The top cover comprises a first top cover and a second top cover with a height difference, whilst the first top cover being above the second top cover, and wherein the first discharging pipe is provided at the first top cover, and the second discharging pipe is provided at the second top cover. At least one of the second discharging pipes is provided at the bottom cover.

The second inlet of the second discharging pipe provided at the bottom cover is not higher than the inner surface of the bottom cover.

Among the first discharging pipes and the second discharging pipes, at least one of the first discharging pipes nests one of the second discharging pipes.

The filter comprises one first discharging pipe and one second discharging pipe and both pipes are provided at the top cover, the first inlet of the first discharging pipe is flush with the inner wall surface of the top cover, the second discharging pipe extends downwards into the filter cavity, and the second inlet is adjacent to the inner wall surface of the bottom cover. The bottom cover has a weight greater than that of the top cover.

DESCRIPTION OF THE EMBODIMENTS

Figure 1:
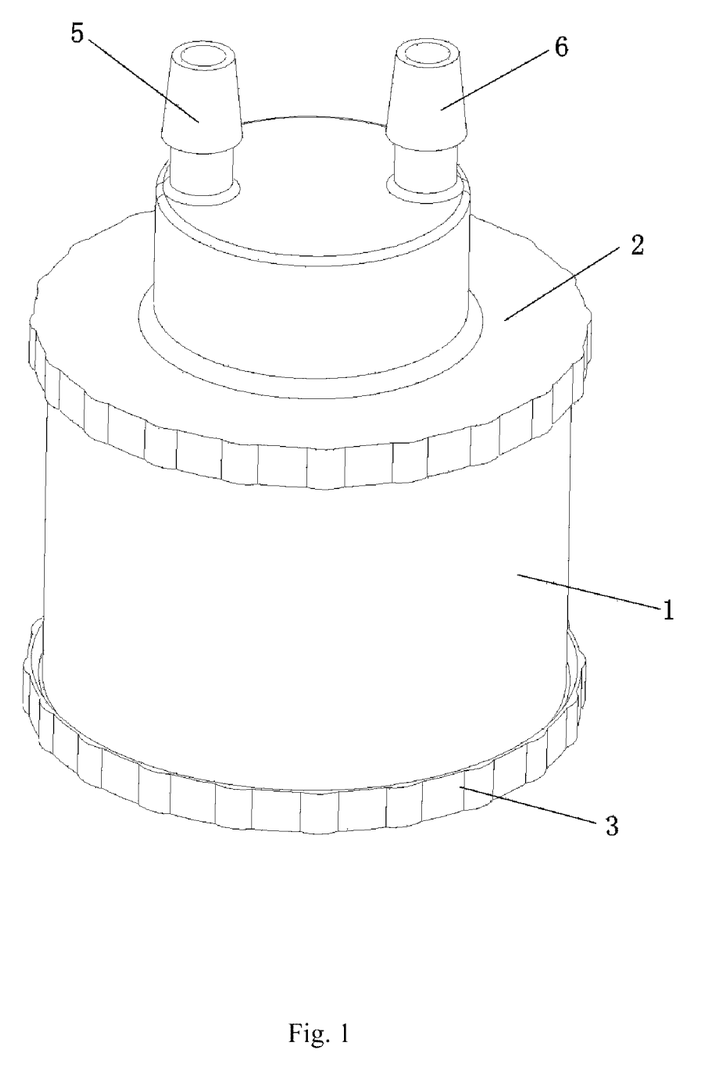
FIG. 1 is a schematic view of the spatial structure of a first embodiment of the filter.
Figure 2:
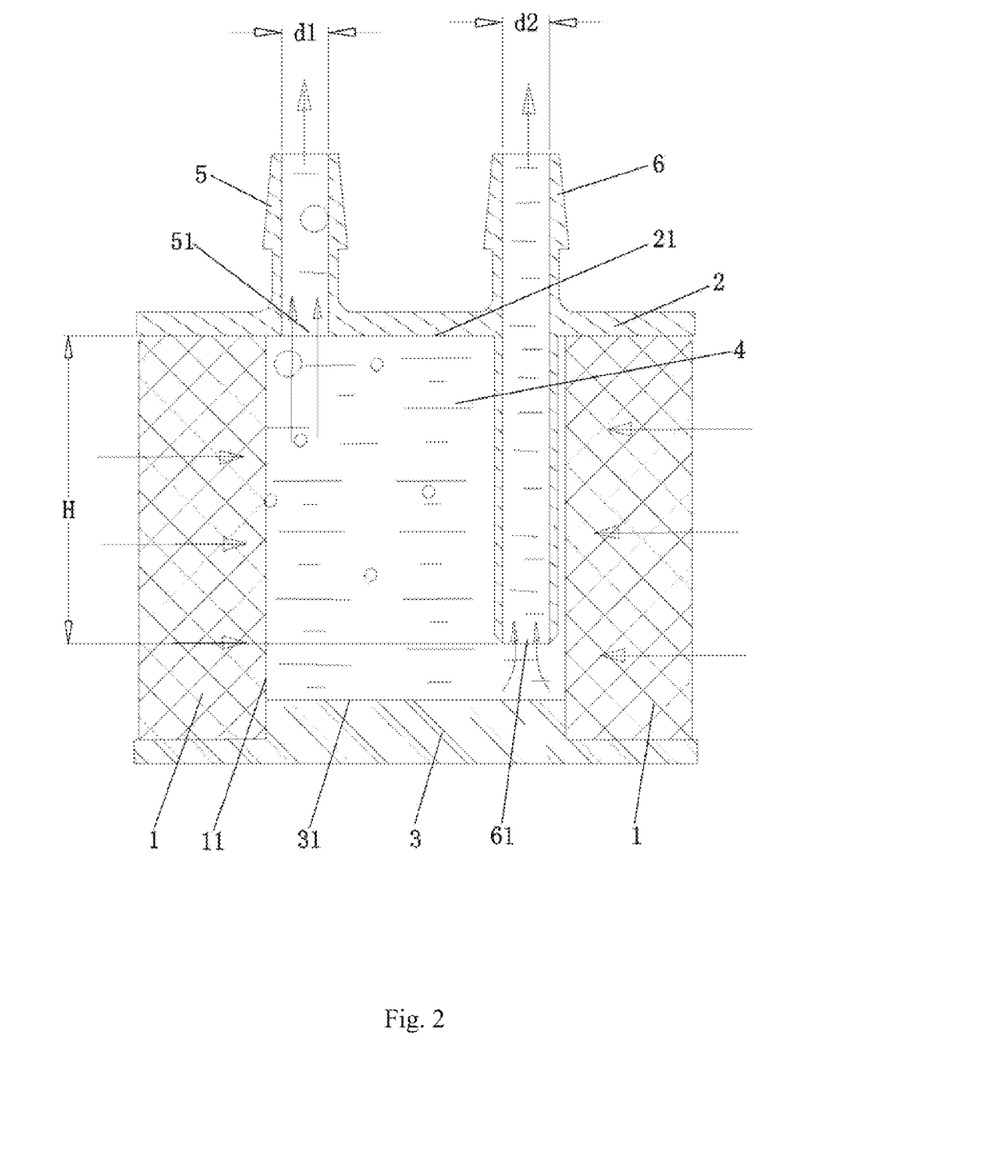
FIG. 2 is a sectional view of the first embodiment of the filter.

As illustrated in FIGS. 1 and 2, the filter of the present embodiment includes a filter core 1, a top cover 2 and a bottom cover 3. The filter core 1 is of a top-to-bottom run-through cylindrical structure, and the top cover 2 and the bottom cover 3 are respectively fixed to the top and the bottom of the filter core 1. The inner wall surface 11 of the filter core 1, the inner wall surface 21 of the top cover 2 and the inner wall surface 31 of the bottom cover 3 define a filter cavity 4. The filter core 1 is provided with a plurality of slots through which the fluid to be filtered can be introduced into the filter cavity, the fluid being a gas-liquid mixture. The top cover 2 is provided with a first discharging pipe 5 and a second discharging pipe 6. The first discharging pipe 5 is vertically fixed to the top cover 2, communicates with the filter cavity 4, and has a first inlet 51 at the bottom through which the fluid flows in, and the first inlet 51 is flush with or slightly above the inner wall surface 21 of the top cover 2 in the gravity direction (namely, the vertical direction), i.e., the first discharging pipe 5 does not extend downwards into the filter cavity 4. The second discharging pipe 6 is vertically fixed to the top cover 2, communicates with the filter cavity 4, and has a second inlet 61 at the bottom through which the fluid flows in, and the second inlet 61 is below the inner wall surface 21 of the top cover 2 in the gravity direction, i.e., the second discharging pipe 6 extends downwards into the filter cavity 4. The second inlet 61 is adjacent to the inner wall surface 31 of the bottom cover 3 but not in direct contact with the inner wall surface 31.

In the gravity direction, the first inlet 51 is situated at a higher position, and the second inlet 61 is situated at a lower position, so that there is a height difference H (H>0) between the first inlet 51 and the second inlet 61.

When the filter is in operation, there are many bubbles generated on the inner wall surface 11 of the filter core 1 due to the negative pressure in the filter cavity 4. When the filter is mounted in the vertical direction, these bubbles will be subjected to a buoyant force of the liquid resulting from the difference in densities of the bubbles and the liquid, so that the bubbles will float up in the filter cavity 4 and naturally accumulate at the highest position in the filter cavity 4, and then enter the first discharging pipe 5 via the first inlet 51 to be discharged. The second inlet 61 is situated at a lower position in the filter cavity 4, such that the liquid comprising a few bubbles or no bubble at the second inlet 61 can be discharged from the second discharging pipe 6, realizing gas-liquid separation. In order to ensure the effect of discharging bubbles, a power pumping device can be provided in the line connected to the first discharging pipe 5 to generate a negative pressure to accelerate the floating up and discharging of the bubbles. A pumping device may also be arranged in the line connected to the second discharging pipe 6 so as to improve the efficiency of discharging the liquid. For example, the pumping device can be implemented by using any suitable conventional or existing pump.

It is easy to realize reliable gas-liquid separation when the filter is placed vertically. However, if the filter is placed slantwise, the function of gas-liquid separation tends to be weakened. In this regard, the bottom cover 3 can be provided with a greater weight than that of the top cover 2, so that the bottom cover 3 can function as a balance weight to ensure that the center of gravity of the filter is always underneath when the filter is in operation, and can be automatically adjusted to the vertical position even if turned over or tilted.

In the present embodiment, the discharging pipe 5 does not extend downwards into the filter cavity 4. The first inlet 51 is situated at the highest position in the filter cavity 4, while the second inlet 61 of the second discharging pipe 6 can be as close to the inner wall surface 31 of the bottom cover 3 as possible, to reinforce the effect of gas-liquid separation.

In the present embodiment, the factors affecting the function of gas-liquid separation include: 1) the flow rates of the first and second discharging pipes 5, 6 which related to the inner diameters d1, d2 of the discharging pipes; 2) the capacity of the filter cavity 4; and 3) the flow rate of the filter core 1. In the design of the filter, in accordance with different fluid permeabilities through the filter core 4 (i.e., the flow rate of the filter core), different inner diameters d1,d2 of the first and second discharging pipes can be designed based on the experimental results to adjust the flow rates of the discharging pipes. At the same time, the capacity of the filter cavity 4 can be designed to realize gas-liquid separation of different effects. For example, 1) what is discharged by the first discharging pipe 5 is all gas, and what is discharged by the second discharging pipe 6 is a liquid without bubbles; and 2) what is discharged by the first discharging pipe 5 is a gas-liquid mixture comprising many bubbles, and what is discharged by the second pipe 6 is a liquid without bubbles. Of course, the second discharging pipe can also discharge a gas-liquid mixture with fewer bubbles. Since what is discharged by the second discharging pipe is a liquid without bubbles or a gas-liquid mixture with fewer bubbles, the second discharging pipe can be connected to the line system susceptible to bubbles, wherein "susceptible" means that the presence of bubbles would have effect on the processing results of the line system to the liquid, The processing results are for example the quantification and detection results of the liquid. The line system can be a liquid sampling line system in an automated biochemical analyzer of the prior art.

Figure 3:
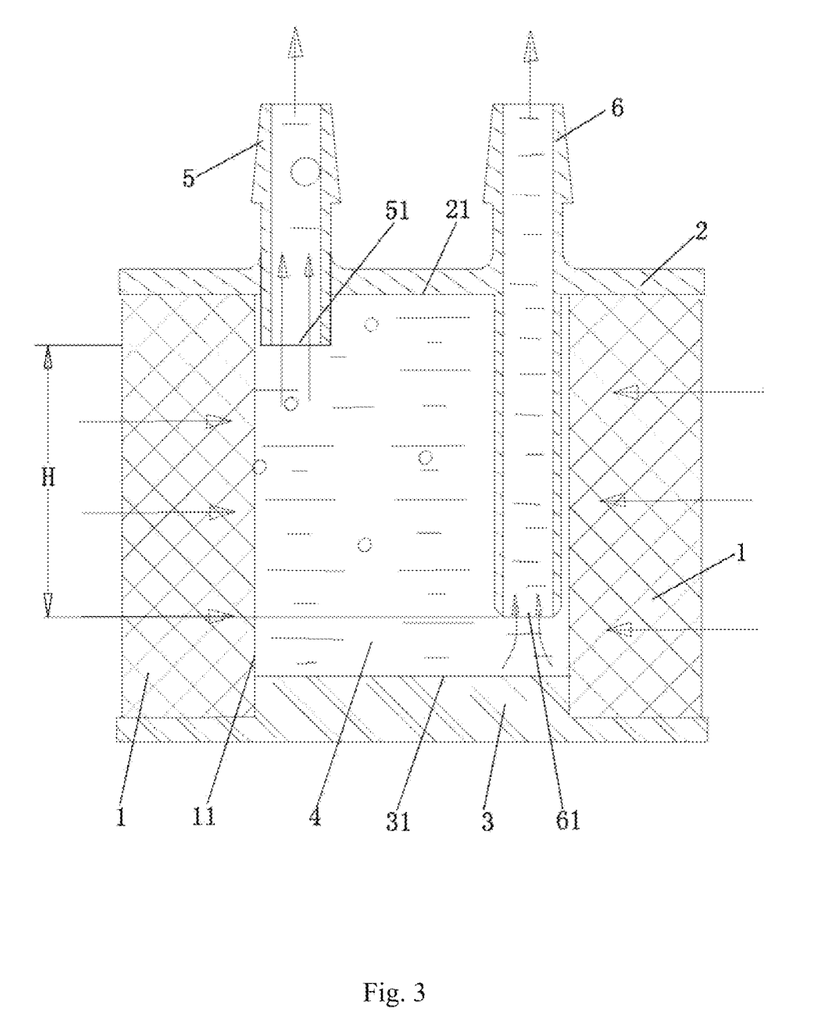
FIG. 3 is a sectional view of a second embodiment of the filter.

FIG. 3 illustrates a second embodiment of the filter. The filter has a filter core 1, a top cover 2 and a bottom cover 3. The inner wall surface 11 of the filter core 1, the inner wall surface 21 of the top cover 2 and the inner wall surface 31 of the bottom cover 3 define a filter cavity 4. The top cover 2 is provided with a first discharging pipe 5 and a second discharging pipe 6, each of the first discharging pipe 5 and the second discharging pipe 6 extending downwards into the filter cavity 4. That is, the first inlet 51 of the first discharging pipe 5 is below the inner wall surface 21 of the top cover 2, the second inlet 61 of the second discharging pipe 6 is below the inner wall surface 21 of the top cover 2, and the first inlet 51 is above the second inlet 61 in the gravity direction with a height difference H therebetween. In order to ensure the gas-liquid separation effect, the first inlet 51 should be as close to the inner wall surface 21 of the top cover 2 as possible, and the second inlet 61 should be as close to the inner wall surface 31 of the bottom cover 3 as possible. The first discharging pipe 5 can discharge bubbles or a gas-liquid mixture with many bubbles, and the second discharging pipe 6 can discharge a liquid or a gas-liquid mixture with fewer bubbles.

Figure 4:
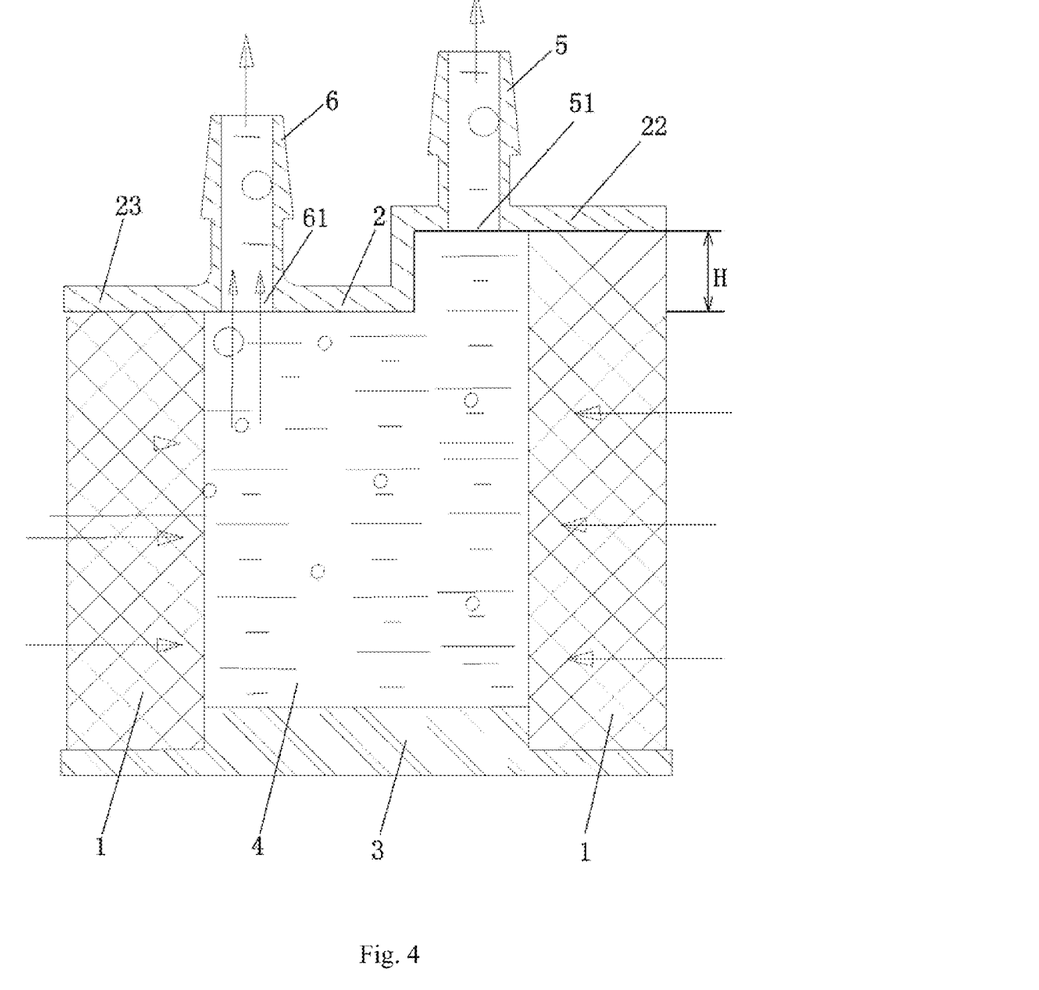
FIG. 4 is a sectional view of a third embodiment of the filter.

FIG. 4 illustrates a third embodiment of the filter. The filter has a filter core 1, a top cover 2 and a bottom cover 3. The inner wall surface of the filter core 1, the inner wall surface of the top cover 2 and the inner wall surface of the bottom cover 3 define a filter cavity 4. The top cover 2 is configured with a stepped shape, having a higher first top cover 22 and a lower second top cover 23. The first top cover 22 is provided with a first discharging pipe 5, and the second top cover 23 is provided with a second discharging pipe 6. Neither of the first discharging pipe 5 and the second discharging pipe 6 extends downwards into the filter cavity 4. The first inlet 51 of the first discharging pipe 5 is above the second inlet 61 of the second discharging pipe 6. Bubbles or a gas-liquid mixture with many bubbles can be discharged through the first discharging pipe 5, while a liquid or a gas-liquid mixture with few bubbles can be discharged through the second discharging pipe 6. In the present embodiment, the first inlet 51 and the second inlet 61 has a height difference H by arranging the first and second discharging pipes 5, 6 at different heights of the top cover 2.

Figure 5:
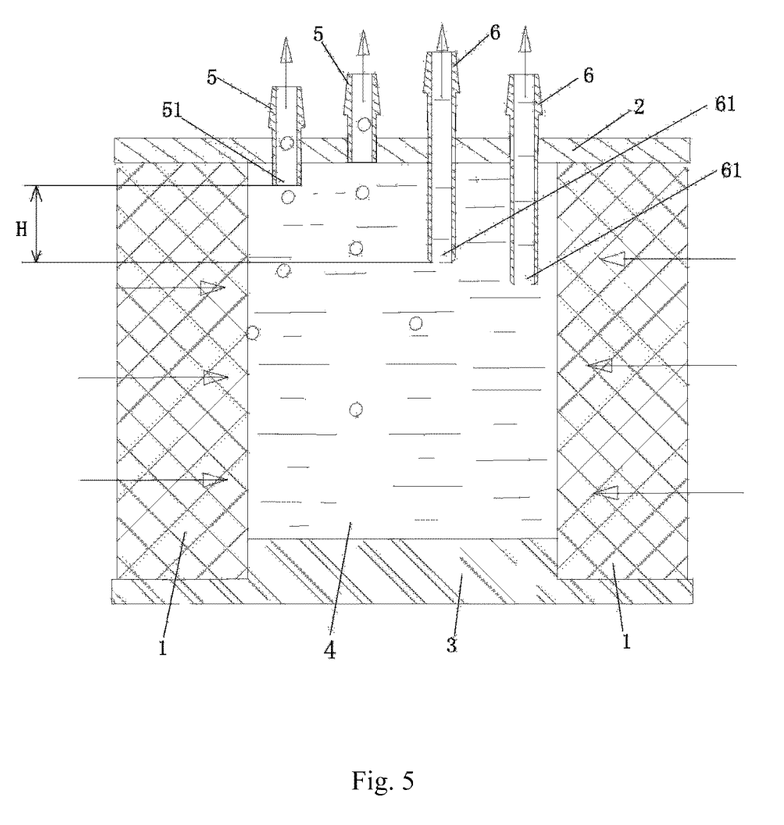
FIG. 5 is a sectional view of a fourth embodiment of the filter.

FIG. 5 illustrates the fourth embodiment of the filter. The filter has a filter core 1, a top cover 2 and a bottom cover 3. The inner wall surface of the filter core 1, the inner wall surface of the top cover 2 and the inner wall surface of the bottom cover 3 define a filter cavity 4. The top cover 2 is provided with two first discharging pipes 5 and two second discharging pipes 6, either of the first discharging pipes 5 having a first inlet 51, and either of the second discharging pipes 6 having a second inlet 61. The lowest first inlet 51 is situated above the highest second inlet 61 in the gravity direction, with a height difference H therebetween. That is, the first inlets 51 are integrally arranged above the second inlets 61.

Figure 6:
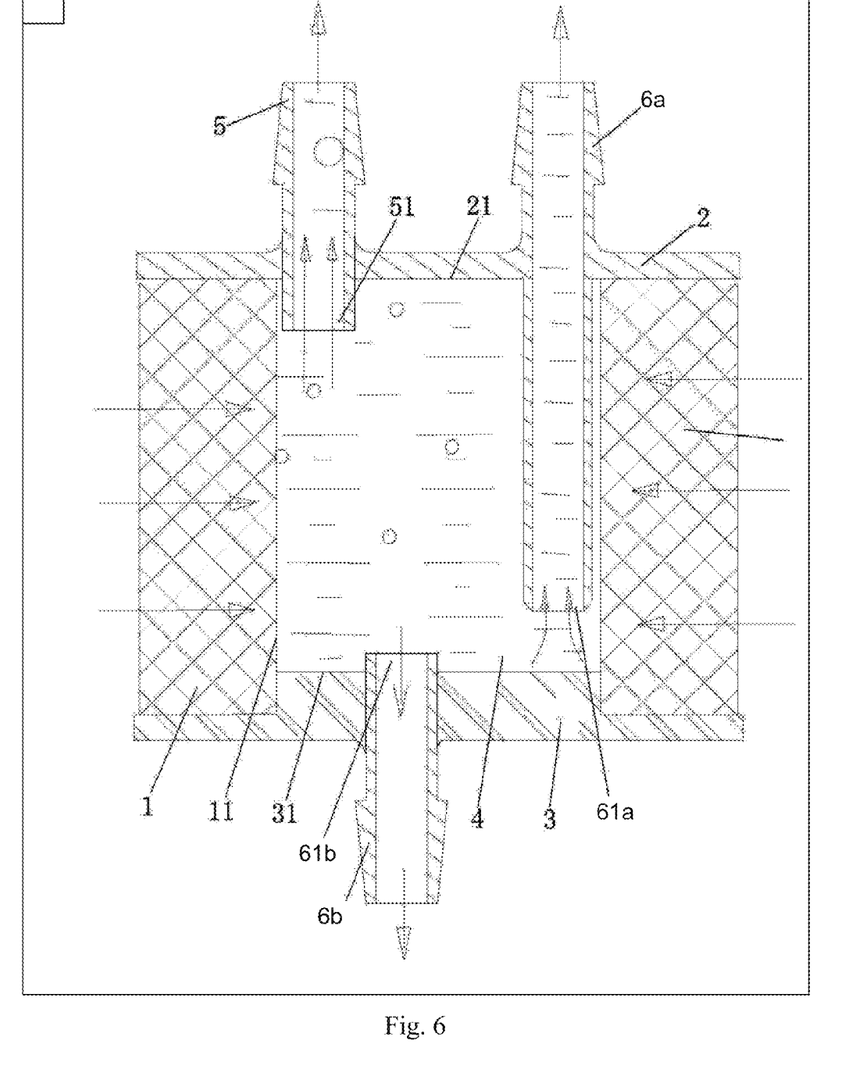
FIG. 6 is a sectional view of a fifth embodiment of the filter.

FIG. 6 illustrates the fifth embodiment of the filter. The filter has a filter core 1, a top cover 2 and a bottom cover 3. The inner wall surface 11 of the filter core 1, the inner wall surface 21 of the top cover 2 and the inner wall surface 31 of the bottom cover 3 define a filter cavity 4. The top cover 2 is provided with one first discharging pipe 5 and one second discharging pipe 6a, and the bottom cover 3 is provided with another second discharging pipe 6b. The first discharging pipe 5 and the second discharging pipe 6a at the top cover 2 both extend downwards into the filter cavity 4, the first inlet 51 of the first discharging pipe 5 being adjacent to the inner wall surface 21 of the top cover 2, and the second inlet 61b of the second discharging pipe 6*b* being adjacent to the inner wall surface 31 of the bottom cover 3. The second discharging pipe 6*b* at the bottom cover 3 extends upwards into the filter cavity 4, the second inlet 61*b* of the second discharging pipe 6*b* being adjacent to the inner wall surface 31 of the bottom cover 3. The first inlet 51 of the first discharging pipe 5 is above the second inlets 61*a* and 61*b* of the two second discharging pipes 6*a* and 6*b* in the gravity direction. The second discharging pipe provided at the bottom cover may not extend upwards into the filter cavity; that is, in some embodiments, the second inlet of the second discharging pipe may not be above the inner wall surface of the bottom cover.

Figure 7:
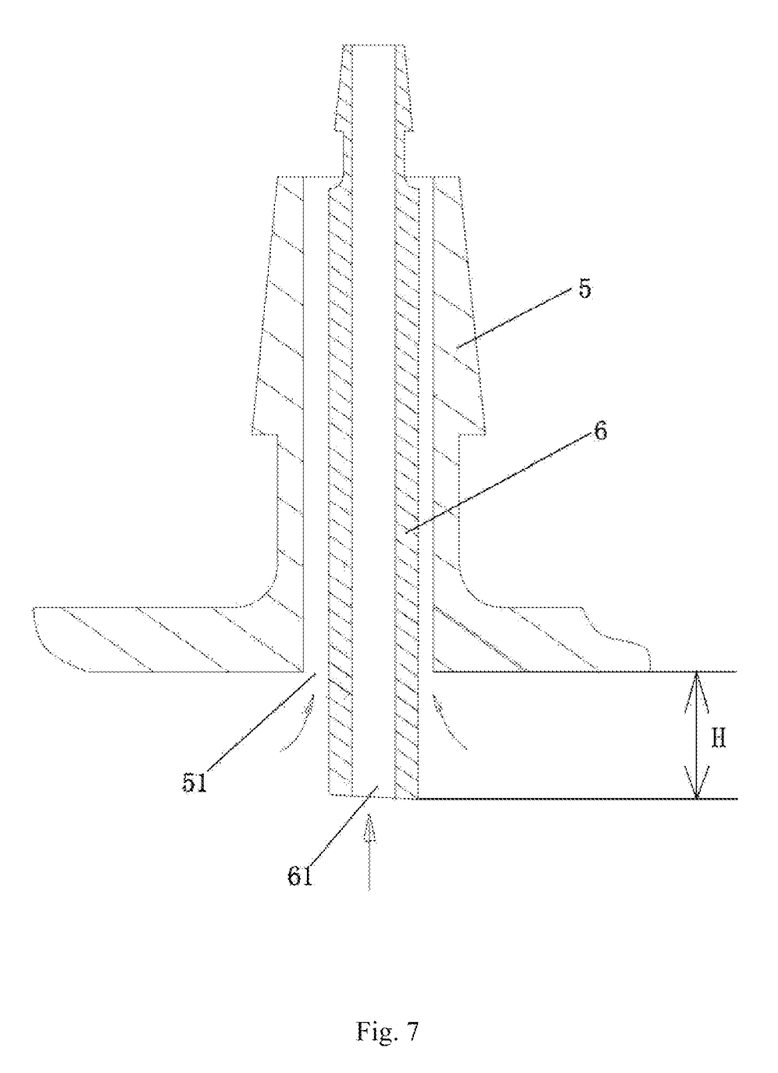
FIG. 7 is a structural schematic view of a sixth embodiment of the filter when the first and second discharging pipes are nested.

FIG. 7 illustrates the sixth embodiment of the filter. The filter has a first discharging pipe 5 and a second discharging pipe 6 provided at the top cover, with the first discharging pipe 5 nesting the second discharging pipe 6. The first inlet 51 of the first discharging pipe 5 is above the second inlet 61 of the second discharging pipe 6. Of course, the second discharging pipe can alternatively nest the first discharging pipe. The first and second discharging pipes can be arranged either coaxially or non-coaxially.

Figure 8:
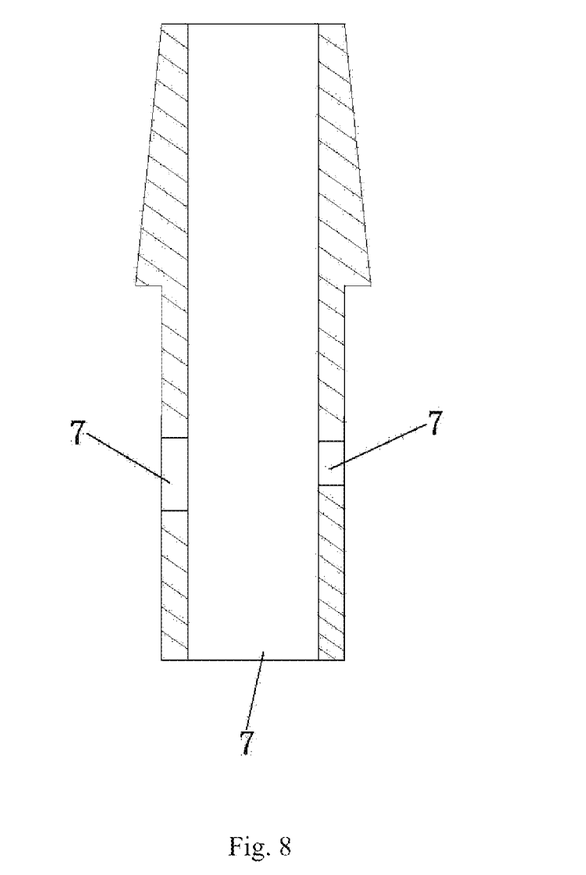
FIG. 8 is a structural schematic view of discharging pipes.

As illustrated in FIG. 8, either the first discharging pipe or the second discharging pipe has two or more inlets 7 through which a fluid flows in. The fluid inlets 7 can each be provided at the bottom or on the wall of the discharging pipe. Each of the inlets of the first discharging pipe is above each of the inlets of the second discharging pipe in the gravity direction. The first and second discharging pipes should extend into the filter cavity if they are respectively provided with two or more inlets.

This filter comprises a filter core, a top cover, a bottom cover, at least one first discharging pipe and at least one second discharging pipe. The filter core has slots through which the fluid mixture to be filtered passes; the top cover and the bottom cover are respectively fixed to the upper portion and the lower portion of the filter core; the inner wall surface of the filter core, the inner wall surface of the top cover and the inner wall surface of the bottom cover define a filter cavity; the first discharging pipes each communicates with the filter cavity and are provided at the top cover, the first discharging pipes each has at least one first inlet through which the fluid flows in; the second discharging pipes each communicates with the filter cavity and is provided at the top cover or the bottom cover, the second discharging pipes each has at least one second inlet through which the fluid flows in; and each of the first inlets is situated above each of the second inlets in the gravity direction. The first inlets are above the second inlets, resulting bubbles or the gas-liquid mixture with many bubbles to be discharged from the first discharging pipes, and the liquid or gas-liquid mixture with fewer bubbles to be discharged from the second discharging pipes, thereby realizing the function of gas-liquid separation without having to add special elements for gas-liquid separation. This filter is simple in structure, able to be reused, low in manufacture cost and reliable in performance. As this filter can effectively realize gas-liquid separation and no or fewer bubbles will enter into the line susceptible to bubbles, the filter can employ a filter core with fairly high filtration precision, thereby ensuring the filtration precision while realizing gas-liquid separation.

In the filter, the second discharging pipe can be connected to a line system susceptible to bubbles, wherein "susceptible" means that the presence of bubbles would have effect on the processing results of the line system to the liquid. The processing results are for example the quantification and detection results of the liquid. The line system can be a liquid quantitative sampling line system in an automated biochemical analyzer, e.g., automated biochemical analyzers of the prior art. The first discharging pipe can be connected to a line system insusceptible to bubbles, wherein "insusceptible" means that the presence of bubbles would have no or minor effect on the treating results of the line system to the liquid. The line system can be cleaning line for cleaning.

In the filter, the first discharging pipe is provided at the top cover. The first discharging pipe may either extend downwards into the filter cavity, or not extend into the filter cavity. In the latter case, the second inlet is flush with or slightly above the inner wall surface of the top cover. The first discharging pipe provided with two or more first inlets needs to extend downwards into the filter cavity. The second discharging pipe is provided at the top cover or the bottom cover and may extend either into or not into the filter cavity (as shown in FIG. 6). In order to improve the effect of gas-liquid separation in certain embodiments, the first inlet should be as close to the inner wall surface of the top cover as possible, or not lower than the inner wall surface of the top cover, and the second inlet should be as close to the inner wall surface of the bottom cover as possible, or not higher than the inner wall surface of the bottom cover. To form a height difference between the first inlet and the second inlet, the first and second discharging pipes can be arranged at different heights of the top cover 2.

In the filter, the bottom cover may have a weight greater than that of the top cover, such that the bottom cover functions as a balance weight. As a result, when the filter is in operation, its center of gravity is always in the lower portion, and the filter can be adjusted automatically to the vertical position even if it is turned over or tilted, which ensures the effect of gas-liquid separation. In this filter, the filter core may be of a top-to-bottom run-through structure, and the top cover and the bottom cover are respectively fixed to the upper portion and the lower portion of the filter core. The filter core may also be of a structure with the upper portion opened and the lower portion closed, in which case the lower portion of the filter core can be considered as the aforesaid bottom cover. In such a structure, the first discharging pipe and the second discharging pipe are arranged at the top cover.

The first and second inlets may be of the shape of circular, square, oval or any other shape allowing the fluid to flow in. The discharging pipe provided with two or more inlets needs to extend into the filter cavity.

The filter can serve to realize filtration and separation of a fluid mixture. The fluid mixture may be either the aforesaid gas-liquid mixture containing gases, or a liquid mixture containing two liquids of different densities. In the latter case, after the mixture to be separated enters into the filter cavity through the filter core, the two liquids are layered due to their different densities, so that the liquid with a minor density rises above, and the liquid with a greater density falls below. In this way, the liquid with a minor density can be drawn by the first discharging pipe, and the liquid with a greater density can be drawn by the second discharging pipe, thereby separating the two fluids.

The filter can be used in either a biochemical analyzer or other applications need fluid filtration and fluid separation.

Although the present invention has been further described above in detail in combination with some particular preferred embodiments, it can not be considered that the present invention is limited to these embodiments. Some alternations or modifications can also occur to those skilled in the art, without departing from the conception of the invention, which alternations or modifications should be deemed to fall into the protection scope of the present invention.

What is claimed is:

1. A filter for filtering fluids, comprising:
   a filter core, wherein the filter core of the filter has a filter element through which a fluid to be filtered passes to become filtered fluid;
   a top cover and a bottom cover, in which the top cover and the bottom cover are respectively fixed to an upper portion and a lower portion of the filter core;
   an inner wall surface of the filter core, an inner wall surface of the top cover, and an inner wall surface of the bottom cover that define a filter cavity that houses the filtered fluid, wherein the filter element has a filtration flow rate entering into the filter cavity;
   a first discharging pipe provided at the top cover and connected to a first discharge pumping device configured to apply negative pressure to the filter cavity, the first discharging pipe at least partially disposed within the filter cavity to form a first passageway to discharge at least a first part of the fluid from the filter cavity, wherein the first discharging pipe has a first inlet through which the fluid flows into the first discharging pipe from the filter cavity;
   a second discharging pipe provided at the top cover and connected to a second discharge pumping device configured to apply negative pressure to the filter cavity, the second discharging pipe at least partially disposed within the filter cavity to form a second passageway to discharge at least a second part of the fluid from the filter cavity, wherein the second discharging pipe has a second inlet through which the fluid flows into the second discharging pipe from the filter cavity, and wherein the first inlet and the second inlet are situated on different planes in a first direction.

2. The filter according to claim 1, wherein the second discharging pipe extends downwards into the filter cavity, and the second inlet of the second discharging pipe is adjacent to the inner wall surface of the bottom cover.

3. The filter according to claim 1, wherein the second discharging pipe extends downwards into the filter cavity, and the first inlet of the first discharging pipe does not extend beyond the inner wall surface of the top cover.

4. The filter according to claim 1, wherein the second inlet of the second discharging pipe is provided at the bottom cover.

5. The filter according to claim 4, wherein the second inlet of the second discharging pipe provided at the bottom cover is not higher than the inner surface of the bottom cover.

6. The filter according to claim 4, wherein the second inlet of the second discharging pipe is adjacent to the inner wall surface of the bottom cover.

7. The filter according to claim 1, wherein the first discharging pipe nests at least a portion of the second discharging pipe.

8. The filter according to claim 1, wherein the first inlet of the first discharging pipe is situated on a first plane that is flush with at least a part of the inner wall surface of the top cover, and the second discharging pipe extends downwards into the filter cavity.

9. The filter according to claim 1, wherein the bottom cover and the top cover are configured to ensure a center of gravity of the filter is in the lower part of the filter.

10. The filter of claim 1, wherein the first discharging pipe and the second discharging pipe are to discharge the fluid that passes through the filter core and comprises a gas-liquid mixture or a mixture of two or more liquids with different densities.

11. The filter of claim 10, in which:
    the first discharging pipe is positioned to discharge the gas-liquid mixture with a first gas-to-liquid ratio,
    the second discharging pipe is positioned to discharge the gas-liquid mixture with a first gas-to-liquid ratio, and
    the first gas-to-liquid ratio is different from the second gas-to-liquid ratio.

12. The filter of claim 1, wherein the second inlet of the second discharging pipe is closer to the inner wall of the bottom cover than the first inlet of the first discharging pipe is.

13. The filter of claim 1, in which the second inlet is positioned proximate the inner wall surface of the bottom cover.

14. The filter of claim 13, in which the one or more flow rate requirements comprises at least one requirement for a flow rate of the filter core, a flow rate of the first discharging pipe, or a flow rate of the second discharging pipe.

* * * * *